United States Patent
Coen et al.

(10) Patent No.: US 11,757,815 B1
(45) Date of Patent: *Sep. 12, 2023

(54) DATA AGGREGATION FROM MULTIPLE ENTITIES

(71) Applicant: TeleTracking Technologies, Inc., Pittsburgh, PA (US)

(72) Inventors: Michael Coen, Morgantown, WV (US); Sunil Nagireddy, McDonald, PA (US); Raghu Ramesh, Wexford, PA (US)

(73) Assignee: TELETRACKING TECHNOLOGIES, INC., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/705,538

(22) Filed: Mar. 28, 2022

Related U.S. Application Data

(63) Continuation of application No. 16/870,457, filed on May 8, 2020, now Pat. No. 11,290,407, which is a continuation of application No. 15/859,544, filed on Dec. 31, 2017, now Pat. No. 10,686,743.

(51) Int. Cl.
| | |
|---|---|
| H04L 51/18 | (2022.01) |
| H04L 67/1097 | (2022.01) |
| H04L 9/40 | (2022.01) |
| G06F 16/25 | (2019.01) |
| H04L 51/56 | (2022.01) |
| G16H 80/00 | (2018.01) |

(52) U.S. Cl.
CPC ............ *H04L 51/18* (2013.01); *G06F 16/258* (2019.01); *H04L 51/56* (2022.05); *H04L 63/102* (2013.01); *H04L 67/1097* (2013.01); *G16H 80/00* (2018.01)

(58) Field of Classification Search
None
See application file for complete search history.

(56) References Cited

U.S. PATENT DOCUMENTS

| 8,861,523 | B2 * | 10/2014 | Hernandez | H04L 45/00 |
| | | | | 370/392 |
| 9,171,344 | B2 * | 10/2015 | Yu | H04L 67/01 |
| 9,578,120 | B1 * | 2/2017 | Evenson | H04L 67/55 |
| 9,584,949 | B2 * | 2/2017 | Korovin | H04W 4/60 |
| 9,760,677 | B2 * | 9/2017 | Yu | G16H 30/20 |
| 9,881,068 | B2 * | 1/2018 | Yeap | G06Q 30/02 |
| 2003/0074248 | A1 * | 4/2003 | Braud | G06Q 10/1093 |
| | | | | 705/7.18 |
| 2003/0105847 | A1 * | 6/2003 | Jennery | H04L 67/34 |
| | | | | 709/223 |

(Continued)

*Primary Examiner* — Lashonda Jacobs-Burton
(74) *Attorney, Agent, or Firm* — FERENCE & ASSOCIATES LLC

(57) ABSTRACT

One embodiment provides a hub of a collecting device that receives messages from entities. The messages are formatted in a message structure that is dependent upon an entity sending the message. The hub analyzes each of the received messages by identifying, from the message structure, information corresponding to an interest of the collecting entity, and discarding information of the message not of interest to the collecting entity. The analysis is agnostic with respect to the entity sending the message and the message structure of the message. The hub performs an action based upon the information corresponding to an interest of the collecting entity.

20 Claims, 2 Drawing Sheets

(56) References Cited

U.S. PATENT DOCUMENTS

| | | | | |
|---|---|---|---|---|
| 2004/0243487 | A1* | 12/2004 | Tien | G06Q 10/087 705/28 |
| 2006/0015563 | A1* | 1/2006 | Judge | H04L 51/212 709/206 |
| 2008/0270438 | A1* | 10/2008 | Aronson | G16H 10/60 714/48 |
| 2011/0119088 | A1* | 5/2011 | Gunn | G16Z 99/00 705/3 |
| 2012/0047214 | A1* | 2/2012 | Daly | H04W 4/02 709/206 |
| 2012/0215860 | A1* | 8/2012 | Bohner | G16H 10/60 709/206 |
| 2012/0226759 | A1* | 9/2012 | Lew | H04W 4/14 709/206 |
| 2013/0080542 | A1* | 3/2013 | Peng | H04L 69/08 709/206 |
| 2014/0006615 | A1* | 1/2014 | Karnik | H04L 63/1441 709/225 |
| 2014/0035726 | A1* | 2/2014 | Schoner | H04W 64/00 340/8.1 |
| 2014/0365241 | A1* | 12/2014 | Dillie | G16H 10/60 705/3 |
| 2017/0004424 | A1* | 1/2017 | Chapman | G16H 70/00 |
| 2017/0372442 | A1* | 12/2017 | Mejias | G16H 40/20 |
| 2018/0024986 | A1* | 1/2018 | Singh | H04L 67/10 704/9 |
| 2018/0101646 | A1* | 4/2018 | Lloyd | G16H 10/60 |
| 2018/0101647 | A1* | 4/2018 | Lloyd | G16H 10/60 |
| 2018/0322946 | A1* | 11/2018 | Ika | G06F 21/6254 |
| 2019/0006030 | A1* | 1/2019 | Mullin | G16H 10/65 |
| 2019/0035027 | A1* | 1/2019 | Ng | G06Q 40/08 |
| 2020/0111549 | A1* | 4/2020 | Lloyd | G06F 16/258 |
| 2022/0223244 | A1* | 7/2022 | Lloyd | G06F 16/33 |

* cited by examiner

DATA AGGREGATION FROM MULTIPLE ENTITIES

CROSS REFERENCE TO RELATED APPLICATIONS

This application is a continuation application of U.S. patent application Ser. No. 16/870,457, filed on May 8, 2020, and entitled "Data Aggregation from Multiple Entities," now U.S. Pat. No. 11,290,407, issued on Mar. 29, 2022, which claims priority to U.S. patent application Ser. No. 15/859,544, filed on Dec. 31, 2017, now U.S. Pat. No. 10,686,743, issued on Jun. 16, 2020, and entitled "Data Aggregation from Multiple Entities," the contents of which are incorporated by reference as if set forth in its entirety.

BACKGROUND

Many entities collect and store information. Not only do some entities collect and store internal information, but it may also collect and store external information, or information received from another entity. As an example, a healthcare enterprise may not only collect information from systems and objects within the healthcare facility, but may also collect information from other healthcare enterprises. Once the information has been collected, the entity may analyze and process the information. Additionally, the entity may store the information for later use. As an example, the collecting entity may capture the information from each of the providing entities and analyze the information in order to determine ways that the collecting entity may additional services to the providing entities.

BRIEF SUMMARY

In summary, one aspect provides a method including: receiving, at a hub of a collecting entity, messages from each of a plurality of entities, wherein each of the messages are published to a single point of the hub, wherein a portion of the messages from at least one of the plurality of entities includes aggregated messages aggregated at the corresponding of the plurality of entities, wherein at least one of the messages includes a message sent directly from a device within one of the plurality of entities; analyzing each of the received messages, wherein the analyzing includes identifying, from the message structure, information corresponding to an interest of the collecting entity, and discarding information of the message not of interest to the collecting entity, wherein the analyzing is agnostic with respect to the entity sending the message and the message structure of the message; and performing an action based upon the information corresponding to an interest of the collecting entity.

Another aspect provides an information handling device, including: a processor; at least one sensor operatively coupled to the processor; a memory device that stores instructions executable by the processor to cause the processor to: receive, at a hub of a collecting entity, messages from each of a plurality of entities, wherein each of the messages are published to a single point of the hub, wherein a portion of the messages from at least one of the plurality of entities includes aggregated messages aggregated at the corresponding of the plurality of entities, wherein at least one of the messages includes a message sent directly from a device within one of the plurality of entities; analyze each of the received messages, wherein the analyzing includes identifying, from the message structure, information corresponding to an interest of the collecting entity, and discarding information of the message not of interest to the collecting entity, wherein the analyzing is agnostic with respect to the entity sending the message and the message structure of the message; and perform an action based upon the information corresponding to an interest of the collecting entity.

A further aspect provides a product, including: a storage device that stores code, the code being executable by a processor and including: code that receives, at a hub of a collecting entity, messages from each of a plurality of entities, wherein each of the messages are published to a single point of the hub, wherein a portion of the messages from at least one of the plurality of entities includes aggregated messages aggregated at the corresponding of the plurality of entities, wherein at least one of the messages includes a message sent directly from a device within one of the plurality of entities; code that analyzes each of the received messages, wherein the analyzing includes identifying, from the message structure, information corresponding to an interest of the collecting entity, and discarding information of the message not of interest to the collecting entity, wherein the analyzing is agnostic with respect to the entity sending the message and the message structure of the message; and code that performs an action based upon the information corresponding to an interest of the collecting entity.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
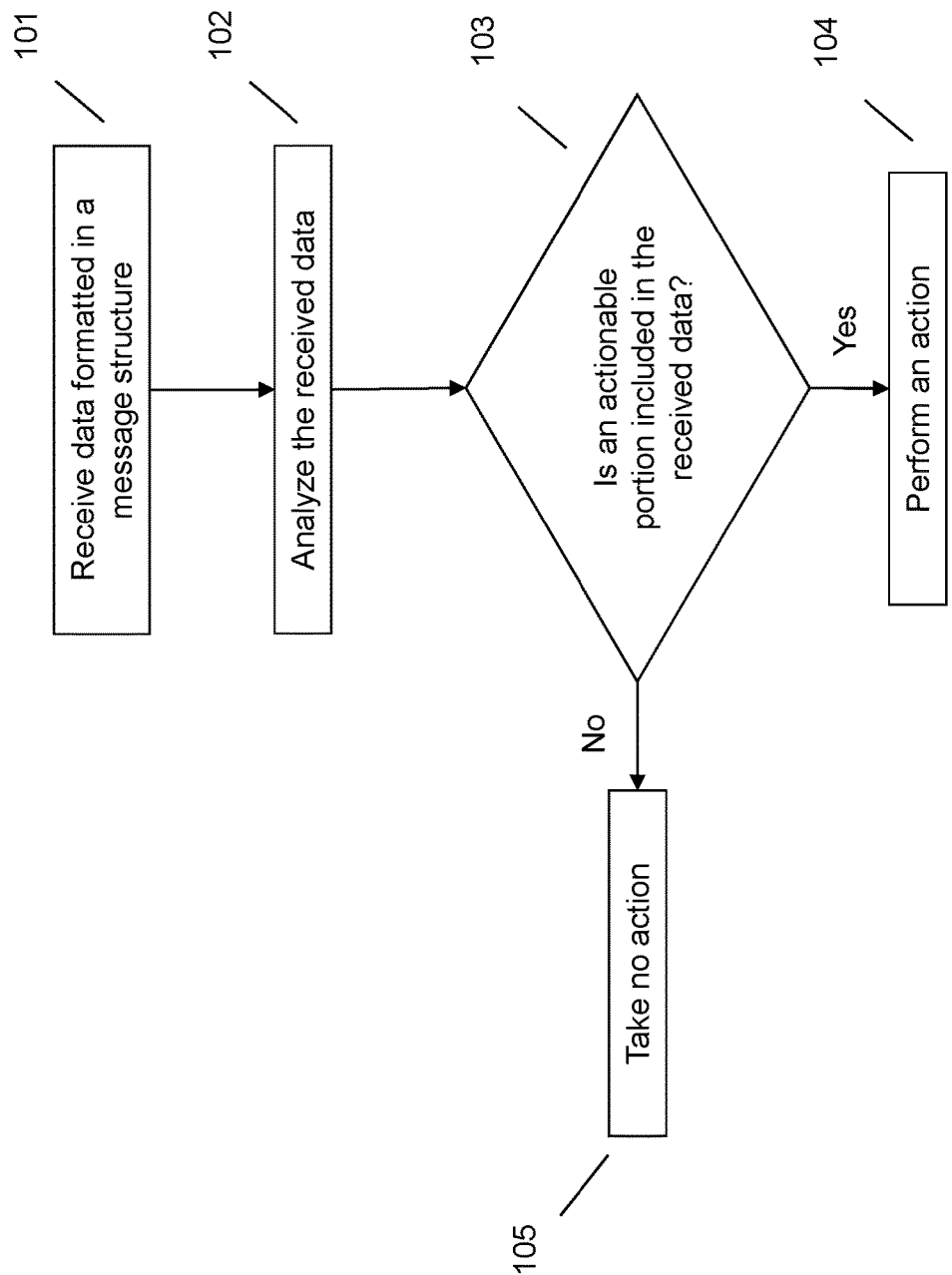
FIG. 1 illustrates an example method of data aggregation from multiple end-points.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

To collect and receive information from multiple entities, the collecting entity (i.e., the entity collecting the information) has to provide a mechanism allowing access by the providing entity (i.e., the entity providing the information). The mechanism may be as simple as requesting that the providing entity manually send the information to the collecting entity, for example, by the providing entity collecting the information and consolidating the information to a single data storage device (e.g., flash drive, CD rom, etc.) and sending the data storage device to the collecting entity. However, this is cumbersome to the providing entity and requires extra manual steps. Therefore, the providing entity may be unwilling to do these steps unless the collecting entity is providing a service that the providing entity requires, for example, technical support, diagnostic services, or the like. Thus, the collecting entity generally tries to make the transference of information from the providing entity as easy and seamless as possible from the perspective of the providing entity.

Thus, another mechanism for transferring the information to the collecting entity is to provide a path or gateway for the providing entity to communicate with the collecting entity, for example, over a network connection, over an Internet connection, or the like. The providing entity can then access the gateway and transfer the information across the gateway to the collecting entity. Additionally, this transference may be an automatic transfer. For example, the providing entity may be connected to the gateway at all times and when information that has been identified as needing transferred to the collecting information is received at the providing entities system, the system automatically sends this information to the collecting entity over the gateway. This method allows a more seamless transfer and does not require extra manual steps by the providing entity.

A problem with this technique occurs from the perspective of the collecting entity. If the collecting entity receives information from multiple providing entities, each of the providing entities will send the information in the preferred format of the providing entity. In other words, the information is sent from the providing entity in a message structure. However, the message structure for one providing entity may not be the same as the message structure of another providing entity. The collecting entity could require that each of the providing entities provide the information in the same message structure, but this is impractical for multiple reasons. First, some of the information may be vendor specific and the providing entity does not have control over the message structure. Second, because no standard exists for these message structures, the providing entity creates a message structure that is convenient for them and would be unlikely to change the structure. Additionally, since it is the collecting entity that wants the information, the providing entity may indicate that the collecting entity either gets the information in the provided message structure or not at all. Thus, the collecting entity has to determine how to identify and analyze the different message structures.

One technique for handling these multiple message structures is that each of the providing entities connects to a specific hub of a system of the collecting entity. This hub is specifically designed to receive messages from that particular providing entity and, thus, is expecting the message structure of the providing entity. The hub can then analyze the message based upon the known message structure and then provide the desired information to the appropriate collecting entity system. However, another problem arises with this multiplicity of hubs, each one for a single providing entity. The provision and maintenance of all of these hubs can become overwhelming to the collecting entity, thereby restricting the scalability of such a system. Additionally, if a message is received with a different message structure that is not expected by the hub, the message is ignored, resulting in a dropped message.

Accordingly, an embodiment provides a method for aggregating data received from a plurality of entities through a plurality of end-points. The systems and methods as described herein provide a single hub that all of the plurality of providing entities communicate with. In other words, using the system and methods as described herein, each of the plurality of providing entities communicate with a single hub and publish messages to a single point. The system of the collecting entity is then able to analyze and process this information in an agnostic manner, meaning that processing and analysis of the messages by the system is independent from the message structure or source of the message.

The system receives, at an aggregate server and from a plurality of entities, data formatted in a message structure. The data received from each of the plurality of entities is received from an end-point associated with the entity sending the data and is received at a single hub. In other words, each of the providing entities sends the information from an end-point of the providing entity into a single hub of the collecting entity system. The system then analyzes the received data by parsing the message structure and extracting at least one actionable portion of the data based upon the parsed message structure. In other words, the system identifies the message structure and determines which portion of the message is of interest to the system. The system then extracts that portion of the message and may discard the remaining portions of the message. Once the actionable portion has been extracted, the system may perform an action based upon that actionable portion. Actions may include triggering a workflow in response to the message, providing a notification in response to the message, generating an alert in response to the message, or the like.

The illustrated example embodiments will be best understood by reference to the figures. The following description is intended only by way of example, and simply illustrates certain example embodiments.

FIG. 1 illustrates a method for obtaining messages from a plurality of entities, regardless of the message structure, into a single hub location and processing the message. At 101 the system receives, at an aggregate server, data having a particular message structure. As explained, the system provides a single aggregate server for all of a plurality of entities. The system may also provide multiple aggregate servers, for example, if the number of messages or providing entities exceeds a volume that are able to be processed and/or stored by a single aggregate server. However, each of the aggregate servers is able to receive messages from a plurality of entities, even though each entity may send messages having different message structures. A providing entity may include an entire facility, a single vendor, an object type, or the like.

As a working example used here throughout to improve readability, the collecting entity will be a healthcare enterprise vendor, for example, a vendor that provides or sources a system used by one or more healthcare enterprises. In this example, the providing entities refer to the healthcare enterprises, vendors of the healthcare enterprises (e.g., vendors that supply tools, systems, etc. that can collect information), objects (e.g., thermometers, blood pressure monitors, heart rate monitors, transport vehicles, etc.), or any other entity/system/object that can capture, access, or otherwise receive information, for example, sensor data, tracking information, scheduling information, staffing information, or the like. While this example, is used here throughout, it should be understood by one skilled in the art that this system can be applied to any collecting entity that collects information from a plurality of providing entities.

For simplicity, the term "hospital" may be used here throughout to refer to a healthcare enterprise. However, it should be understood by one skilled in the art that this term may refer to any healthcare enterprise, for example, long-term care facility, emergency department, healthcare staffing area, and the like. Additionally, healthcare enterprise is intended to describe an entire enterprise under a single healthcare provider. In other words, a healthcare enterprise may include one or more buildings that may be located in one or more buildings in one or more geographical areas. Each of the departments within the healthcare enterprise may be referred to herein as a "facility". For example, the emergency department may be one facility, the long-term care department may be another facility, the in-patient department may be another facility, and the like. Each of the facilities may be located in separate buildings or may be located within the same building. For example, an emergency department may be located within the same building as an in-patient care facility.

The data or information received at the aggregate server of the healthcare enterprise vendor is formatted in a message structure based upon the providing entity. For example, one vendor may provide messages having one message structure, while another vendor provides messages having a different message structure. In other words, the message structure is dependent on the entity sending the data. The message structures may be different across vendors, healthcare enterprises, device types, and the like. Additionally, messages of the same type may even have different message structures. For example, a message relating to tracking a patient sent by one providing entity may have a message structure that is different from a different providing entity sending a message relating to tracking a patient. By coincidence or coordination, some messages from different providing entities may have the same message structure. In other words, each providing entity does not have to provide messages having a message structure unique from each other providing entity.

Each of the providing entities may provide the data from an end-point associated with the entity sending the data. As an example, when a providing entity provides information to the healthcare enterprise vendor, the providing entity may send the information across a network, for example, an intranet network, an Internet network, or the like. In other words, each of the providing entities may have a particular communication channel that the providing entity uses to communicate with the collecting entity. As an example, to communicate information to the collecting entity, the providing entity may access a uniform resource locator (URL) that is assigned to the providing entity. The information may then be sent across this secure communications channel and received at a communications port of the collecting entity. Thus, when the information is received at the aggregate server of the collecting entity, the server can identify which providing entity provided the information. However, all of the plurality of providing entities communicate with a single hub, as opposed to communicating with a hub specifically assigned to the providing entity as in traditional systems. Thus, all the messages from all of the plurality of providing entities are published to a single point. However, each of the plurality of providing entities may communicate to this single point using a communications port assigned to that providing entity. This communications port may correspond to the end-point of that providing entity.

In some cases, a facility may aggregate all the information collected within the facility and send this information to the collecting entity. In other words, the facility acts as an initial data aggregator and the collecting entity only receives a single stream of information from that facility. Alternatively, each information source within a facility may have a direct communication connection with the collecting entity. Thus, the collecting entity may receive multiple communication streams from a single facility. As an example, a blood pressure monitor within a hospital may, instead of sending the information to the hospital system to be aggregated with all the other information within the hospital, directly communicate the information to the collecting entity. Similarly, each other object or system within the hospital may also directly communicate the information to the collecting entity.

At 102 the system may analyze the received data to identify one or more portions of interest to the collecting entity. Portions of interest may include those portions of the message which provide desired information to the collecting entity. For example, if the collecting entity is interested in tracking information, the system may identify the portions of the message that correspond to tracking information or information associated with the tracking information. The system may then discard information that is not of interest to the collecting entity. As an example, if the message includes information related to tracking information, the information of interest in this example, and also includes a message header that identifies a message identifier, timestamp, vendor type, and the like, the system may identify that the message identifier and vendor type is not of interest and may discard this information. In other words, the message may include information that is useful to, for example, the vendor, but is not used by any other entity so is discarded.

The analysis techniques used to analyze the received data may include techniques that are agnostic to either the providing entity or the message structure. In other words, the system can analyze the message regardless of how the message is structured or which entity has sent the message. When the message is received, the system does not have to know what the structure of the message is in order to analyze the message. Therefore, the system can analyze messages of any structure, which allows the system to analyze messages even if the messages are of a structure that is not previously known to the system, for example, if the message structure gets jumbled, in the case of a new providing entity not previously known to the system, in the case that a known providing entity modifies the structures of messages sent, or the like. In other words, rather than having a single hub that is dedicated to receiving and processing messages of a particular structure from a particular providing entity, the described system can receive all messages from all entities no matter the message structure and still analyze and process the message, thereby making the system message structure and providing entity agnostic.

To analyze the received information the system may parse the message to determine or identify the message structure. Part of parsing the message to identify the message structure may include identifying the entity that sent the message. For example, the message may include information that indicates the providing entity. As another example, the system may identify which communication port that the message was received at. This communications port can then be correlated to the end-point associated with the providing entity. This association can then be used by the system to identify the providing entity. Since each providing entity provides messages having a message structure, the message structure provided by that entity may be previously known. Thus, once the providing entity is known, the system may then know the structure of the message based upon identifying the providing entity.

The system may also use other techniques to identify the structure of the message. For example, certain information may be included in certain predetermined parts of a message. As an example, message identifiers may always be included in the message header. Thus, when the system identifies a part of the message as a message identifier, the system may then identify the portion of the message including the message identifier as the message header. Parsing the message may also include parsing the content of the message itself, for example, using conventional message parsing techniques, to identify words, data structures (e.g., date formats, identification formats, etc.), or other information included in the message.

Once the system has identified and parsed the message structure the system may extract at least one actionable portion of the data, where the actionable portion is identified based upon the message structure. In other words, the system knows which portion of the message structure includes the information of interest to the collecting entity. Once the message structure is identified, the system can extract this information of interest from the appropriate location within the message. If the system determines at 103 that no actionable information or portions are included in the message, the system may take no action with regard to extraction of a portion of the message at 105. Taking no action may include discarding the message, storing the message without extracting any information from the message, or the like. If, however, the system determines at 103 that the message includes actionable information or portions, the system may extract that portion and perform an action responsive to the actionable portion at 104.

Performing an action may include providing a notification, triggering a workflow, generating an alert, or the like, in response to the message. In other words, the system is able to process the messages in real-time and respond to the message in real-time by performing some action that is responsive to the message. Triggering a workflow may include updating a system in response to the message or causing some action to be taken by another system. As an example, if the message is related to patient tracking, upon receipt of the message the system may identify that the message includes information related to a new location of the patient. Thus, the system may trigger a workflow that updates a patient tracking system. As another example, if the message is related to use of a consumable object, the system may update a consumables inventory system with the use of the consumable object. As a final example, if the message is related to timing information with regard to performance of a procedure, the system may update a system that tracks information related to how long a procedure takes to perform.

Providing a notification or generating an alert may include providing a notification to a user who monitors the system. Using the example of using a consumable object, the system may provide a notification to the user that the consumable product has been used. As another example, if the message identifies opening of a locked door, the system may provide a notification that the door has been opened. Generating an alert may include generating a notification that includes an actionable item. In other words, a notification may merely notify the user that something has occurred, while an alert may include not only the notification by may also include instructions for performing an action in response to the notification. As an example, if the locked door that is opened is opened by someone who is unauthorized, the alert may not only notify the user of the opening of the door but may also include a notification that the user is unauthorized, thereby implying an actionable item by the user.

The system may also store the received data at the aggregate server or a data storage location associated with or accessible by the aggregate server. In storing the information, the system may keep the information separate based upon the providing entity. For example, if the providing entity is a particular hospital facility, the system may store all the information associated with that hospital facility in a data storage location that is assigned to that hospital facility. All the other hospital facilities would also have unique data storage locations. As another example, if the providing entity is a particular device type, the system may store all the information associated with that device type, even if different hospitals have the same device type, in a data storage location that is assigned to that device type. All other device types would have a unique data storage location. Additionally, the system may store the data into multiple data storage locations. For example, the message may be duplicated and stored in multiple data storage locations, for example, a data storage location associated with the facility and a data storage location associated with the device type.

Storing the messages in unique storage locations based upon a parameter (e.g., providing entity, device type, vendor, message receipt time, etc.) allows the system to perform additional downstream actions. For example, if the providing entity requests information associated with the messages, the collecting entity can provide the information in relation to just the messages received by that providing entity. Additionally, the collecting entity may provide a comparison of information between two or more providing entities. For example, if the providing entities are interested in what the typical time is for performing a specific procedure, the collecting entity can access the information to make this comparison and provide these analytics to the providing entity.

The various embodiments described herein thus represent a technical improvement to current systems for receiving data from a plurality of entities, each having its own message structure. Rather than requiring a separate hub for each of the entities, the systems and methods as described herein provides a single agnostic hub that can process a message no matter the message structure. Such a system allows scalability of the system to work for any number of providing entities. Additionally, since the system is message agnostic, the system can process messages no matter the message structure which results in fewer dropped messages. Additionally, the message agnostic system allows for processing of messages from new entities that may have a message structure different from any other message structure without requiring expensive hardware or software to process the message.

While various other circuits, circuitry or components may be utilized in information handling devices, with a computer, server, client device or the like, an example device that may be used in implementing one or more embodiments includes a computing device in the form of a computer 200. This example device may be a server used in one of the systems in a hospital network, or one of the remote computers connected to the hospital network. Components of computer 200 may include, but are not limited to, a processing unit 220, a system memory 230, and a system bus 222 that couples various system components including the system memory 230 to the processing unit 220. Computer 200 may include or have access to a variety of computer readable media, including databases. The system memory 230 may include non-signal computer readable storage media, for example in the form of volatile and/or nonvolatile memory such as read only memory (ROM) and/or random access memory (RAM). By way of example, and not limitation, system memory 230 may also include an operating system, application programs, other program modules, and program data.

A user can interface with (for example, enter commands and information) the computer 200 through input devices 250. A monitor or other type of device can also be connected to the system bus 222 via an interface, such as an output interface 260. The computer may include a database 240. In addition to a monitor, computers may also include other peripheral output devices. The computer 200 may operate in a networked or distributed environment using logical connections to one or more other remote device(s) 280 such as other computers. The logical connections may include network interface(s) 270 to a network, such as a local area network (LAN), a wide area network (WAN), and/or a global computer network, but may also include other networks/buses.

Figure 2:
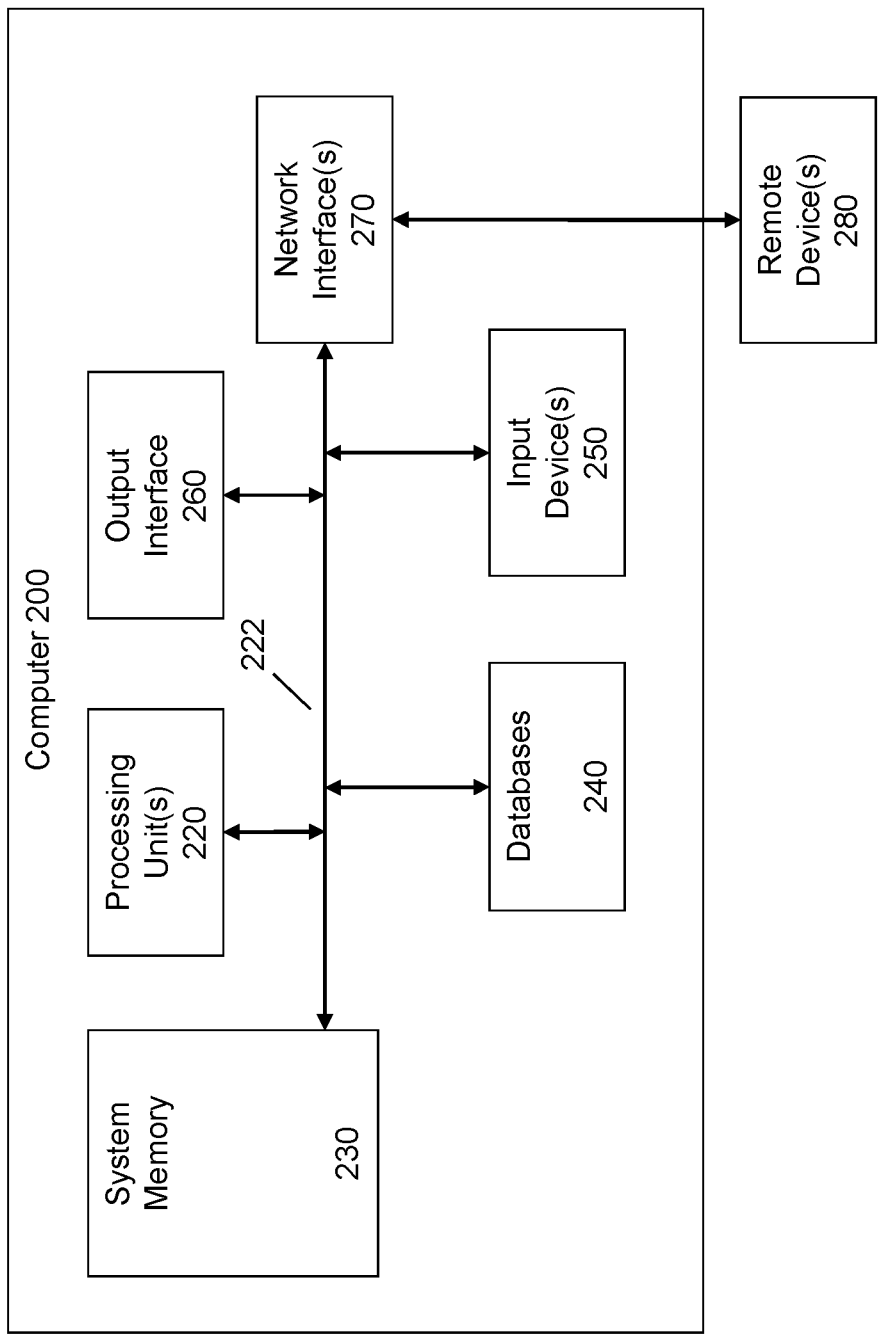
FIG. 2 illustrates an example of device circuitry.

Information handling device circuitry, as for example outlined in FIG. 2, may be used in client devices such as a personal desktop computer, a laptop computer, or smaller devices such as a tablet or a smart phone. In the latter cases, i.e., for a tablet computer and a smart phone, the circuitry outlined in FIG. 2 may be adapted to a system on chip type circuitry. The device, irrespective of the circuitry provided, may provide and receive data to/from another device, e.g., a server or system that coordinates with various other systems. As will be appreciated by one having ordinary skill in the art, other circuitry or additional circuitry from that outlined in the example of FIG. 2 may be employed in various electronic devices that are used in whole or in part to implement the systems, methods and products of the various embodiments described herein.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method comprising:
   receiving, at a hub of a collecting entity, messages from each of a plurality of entities, wherein messages received from different of the plurality of entities have message structures different than other of the plurality of entities, wherein all of the messages from the plurality of entities are published to a single point of the hub utilizing a communications port assigned to each of the plurality of entities, wherein a portion of the messages from at least one of the plurality of entities comprises aggregated messages aggregated at a corresponding of the plurality of entities, wherein at least one of the messages comprises a message sent directly from a device within one of the plurality of entities;

analyzing each of the received messages, wherein the analyzing comprises identifying, from a structure of the message, information corresponding to an interest of the collecting entity, and discarding information of the message not of interest to the collecting entity, wherein the analyzing is agnostic with respect to an entity of the plurality of entities sending the message and the structure of the message; and performing an action based upon the information corresponding to an interest of the collecting entity.

2. The method of claim 1, wherein the structure of the message is dependent on the entity of the plurality of entities sending the message.

3. The method of claim 1, wherein the analyzing comprises parsing the structure of the message.

4. The method of claim 3, wherein the analyzing comprises identifying elements of the messages based upon the parsed structure of the message.

5. The method of claim 1, wherein the action is selected from the group consisting of: providing a notification and triggering a workflow.

6. The method of claim 1, wherein the structure of the message is identified based upon a communications port of receipt of the message that is correlated to an end-point of an entity.

7. The method of claim 1, further comprising storing the received message at the collecting entity.

8. The method of claim 7, wherein each of the plurality of entities comprises a facility and wherein the storing comprises storing messages received from each entity separately from messages received from each other entity.

9. The method of claim 7, wherein each of the plurality of entities comprises a device type and wherein the storing comprises storing messages received from each entity separately from messages received from each other entity.

10. The method of claim 1, wherein the structure of the message received is different for different entities within the plurality of entities.

11. An information handling device, comprising:
a processor;
at least one sensor operatively coupled to the processor;
a memory device that stores instructions executable by the processor to cause the processor to:
receive, at a hub of a collecting entity, messages from each of a plurality of entities, wherein messages received from different of the plurality of entities have message structures different than other of the plurality of entities, wherein all of the messages from the plurality of entities are published to a single point of the hub utilizing a communications port assigned to each of the plurality of entities, wherein a portion of the messages from at least one of the plurality of entities comprises aggregated messages aggregated at a corresponding of the plurality of entities, wherein at least one of the messages comprises a message sent directly from a device within one of the plurality of entities;
analyze each of the received messages, wherein the analyzing comprises identifying, from a structure of the message, information corresponding to an interest of the collecting entity, and discarding information of the message not of interest to the collecting entity, wherein the analyzing is agnostic with respect to an entity of the plurality of entities sending the message and the structure of the message; and
perform an action based upon the information corresponding to an interest of the collecting entity.

12. The information handling device of claim 11, wherein the structure of the message is dependent on the entity of the plurality of entities sending the message.

13. The information handling device of claim 11, wherein the analyzing comprises parsing structure of the message; and
wherein the analyzing comprises identifying elements of the messages based upon the parsed structure of the message.

14. The information handling device of claim 11, wherein the action is selected from the group consisting of: providing a notification and triggering a workflow.

15. The information handling device of claim 11, wherein the structure of the message is identified based upon a communications port of receipt of the message that is correlated to an end-point of an entity.

16. The information handling device of claim 11, further comprising storing the received message at the collecting entity.

17. The information handling device of claim 16, wherein each of the plurality of entities comprises a facility and wherein the storing comprises storing messages received from each entity separately from messages received from each other entity.

18. The information handling device of claim 16, wherein each of the plurality of entities comprises a device type and wherein the storing comprises storing messages received from each entity separately from messages received from each other entity.

19. The information handling device of claim 11, wherein the structure of the message received is different for different entities within the plurality of entities.

20. A product, comprising:
a storage device that stores code, the code being executable by a processor and comprising:
code that receives, at a hub of a collecting entity, messages from each of a plurality of entities, wherein messages received from different of the plurality of entities have message structures different than other of the plurality of entities, wherein all of the messages from the plurality of entities are published to a single point of the hub utilizing a communications port assigned to each of the plurality of entities, wherein a portion of the messages from at least one of the plurality of entities comprises aggregated messages aggregated at a corresponding of the plurality of entities, wherein at least one of the messages comprises a message sent directly from a device within one of the plurality of entities;
code that analyzes each of the received messages, wherein the analyzing comprises identifying, from a structure of the message, information corresponding to an interest of the collecting entity, and discarding information of the message not of interest to the collecting entity, wherein the analyzing is agnostic with respect to an entity of the plurality of entities sending the message and the structure of the message; and code that performs an action based upon the information corresponding to an interest of the collecting entity.

\* \* \* \* \*

UNITED STATES PATENT AND TRADEMARK OFFICE
CERTIFICATE OF CORRECTION

| | |
|---|---|
| PATENT NO. | : 11,757,815 B1 |
| APPLICATION NO. | : 17/705538 |
| DATED | : September 12, 2023 |
| INVENTOR(S) | : Michael Coen et al. |

It is certified that error appears in the above-identified patent and that said Letters Patent is hereby corrected as shown below:

On the Title Page

Item (72) the listing of inventors should read:
Michael Coen, Morgantown, WV (US);
Sunil Nagireddy, McDonald, PA (US);
Raghu Ramesh, Wexford, PA (US);
Ratna Divya Kanthi Bejjam, Bridgeville, PA (US)

Signed and Sealed this
Twenty-eighth Day of May, 2024

Katherine Kelly Vidal
*Director of the United States Patent and Trademark Office*